(12) United States Patent
Pienknagura

(10) Patent No.: US 8,372,137 B2
(45) Date of Patent: Feb. 12, 2013

(54) INTRAVASCULAR STENT WITH INVERTED END RINGS

(75) Inventor: Carla Rosa Pienknagura, San Carlos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 40 days.

(21) Appl. No.: 13/151,921

(22) Filed: Jun. 2, 2011

(65) Prior Publication Data

US 2011/0230959 A1    Sep. 22, 2011

Related U.S. Application Data

(62) Division of application No. 11/751,506, filed on May 21, 2007, now Pat. No. 7,959,665.

(51) Int. Cl.
*A61F 2/06* (2006.01)

(52) U.S. Cl. ...................................................... 623/1.16

(58) Field of Classification Search .................. 623/1.11, 623/1.15, 1.16
See application file for complete search history.

(56) References Cited

U.S. PATENT DOCUMENTS 6,540,775 B1    4/2003    Fischell et al.

*Primary Examiner* — Victor Nguyen
(74) *Attorney, Agent, or Firm* — Fulwider Patton LLP

(57) ABSTRACT

The invention is directed to an expandable stent for implanting in a body lumen, such as a coronary artery, peripheral artery, or other body lumen. The invention provides for an intravascular stent having a plurality of cylindrical rings connected by undulating links. A plurality of inverted cylindrical end rings can be coupled at least in part to a plurality of adjacent cylindrical rings in the form of mirror images such that a symmetrical configuration is present on at least one of a proximal end and a distal end of the stent. The stent has a high degree of flexibility in the longitudinal direction, yet has adequate vessel wall coverage and radial strength sufficient to hold open an artery or other body lumen. The inverted end ring configuration of the stent aims at reducing the stent-to-shoulder distance as well as delivering therapeutic drug to the peri-stent area while maintaining a pristine stent deployment.

3 Claims, 14 Drawing Sheets

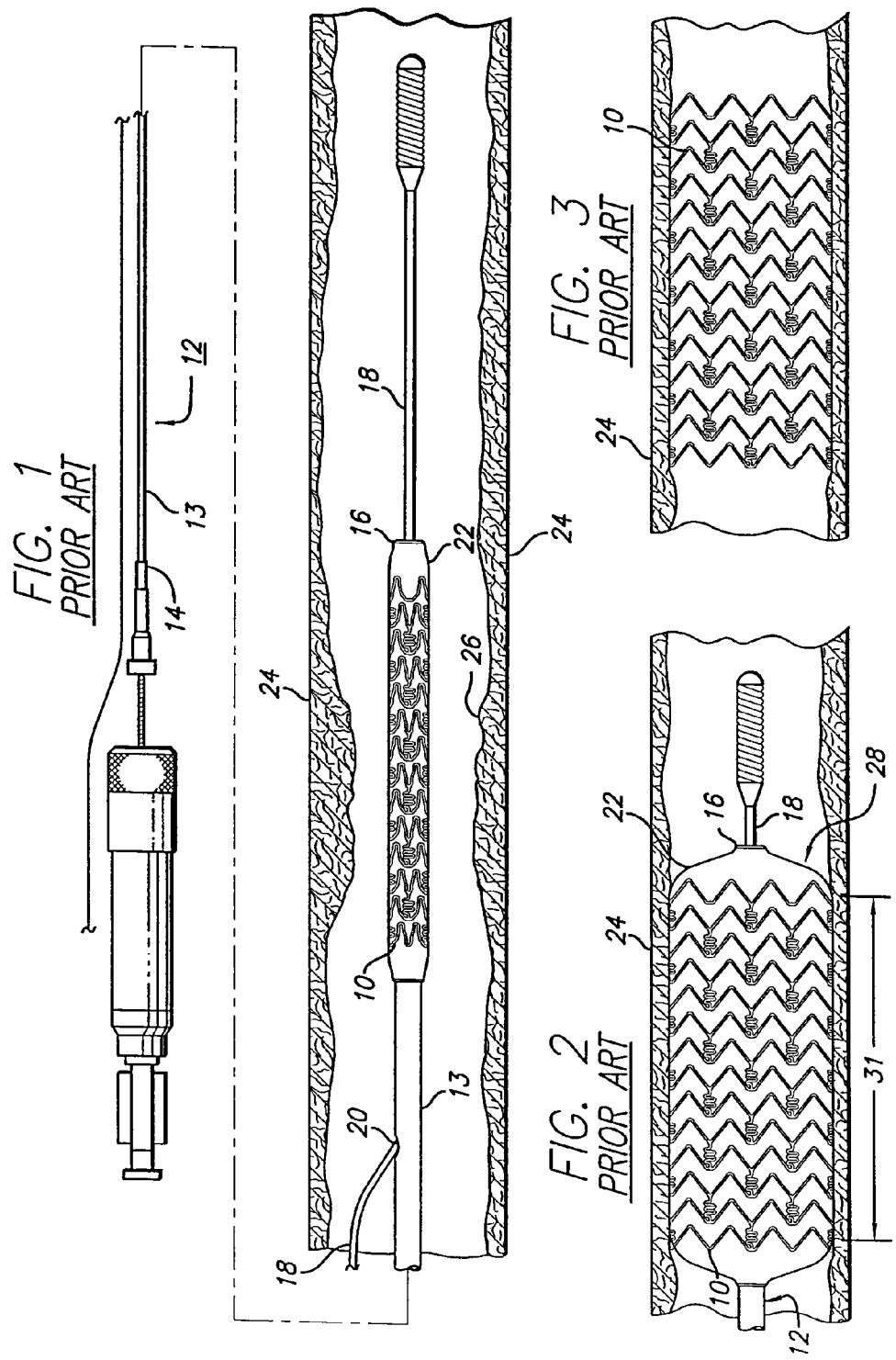

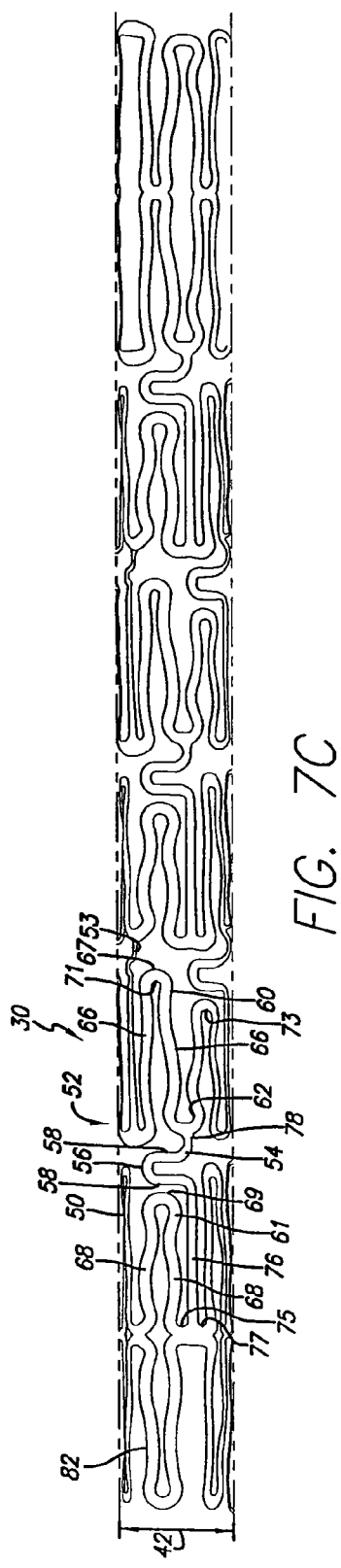
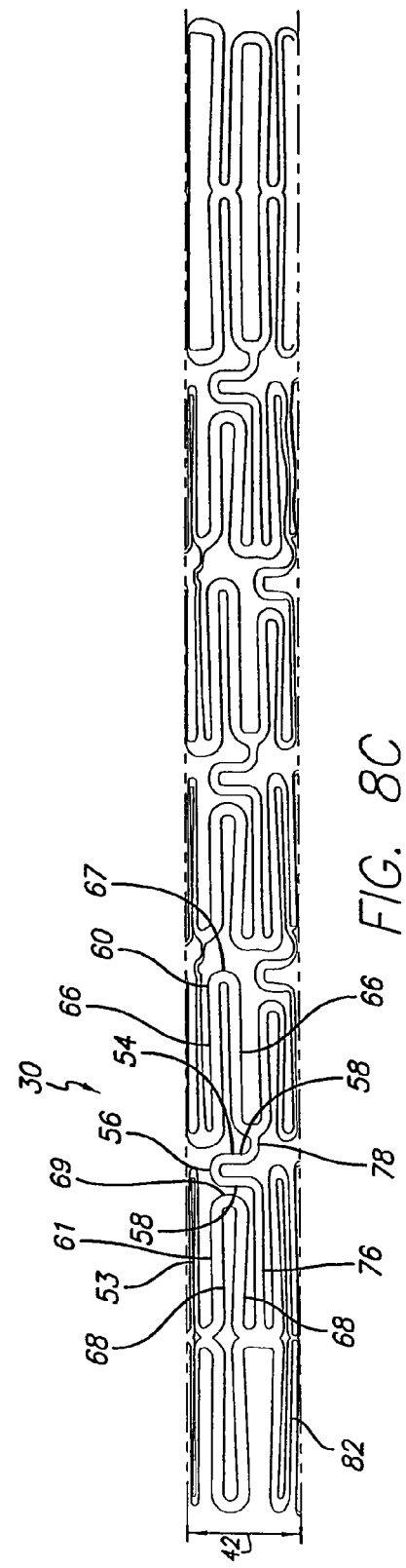

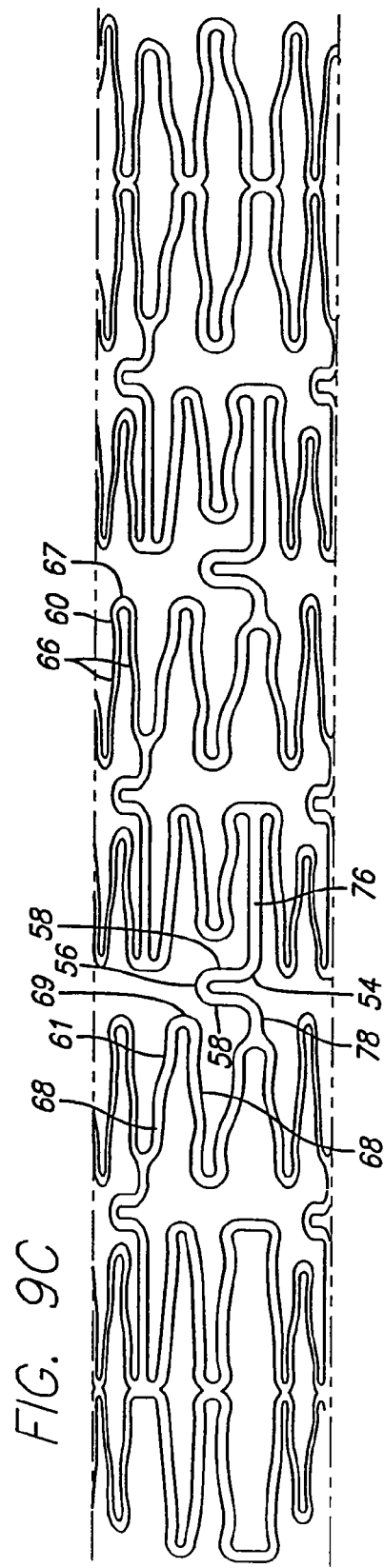
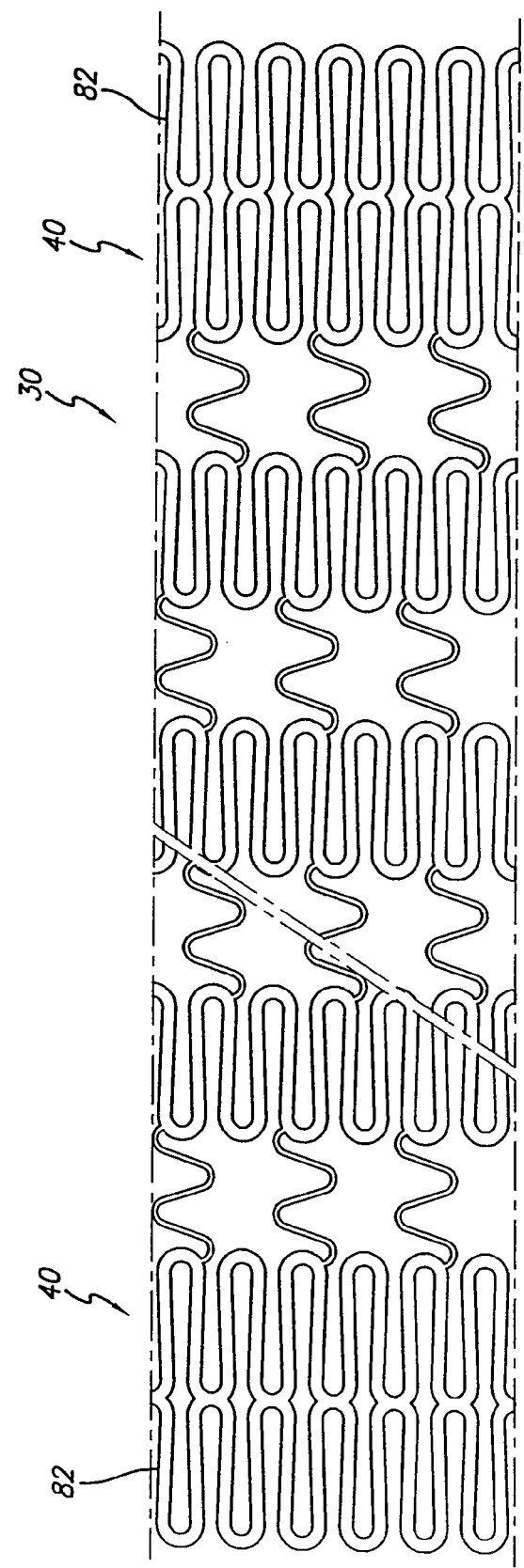

INTRAVASCULAR STENT WITH INVERTED END RINGS

CROSS-REFERENCE TO RELATED APPLICATIONS

This is a divisional application of co-pending U.S. Ser. No. 11/751,506 filed May 21, 2007, which is a division of U.S. Ser. No. 10/631,159 filed Jul. 12, 2004, now abandoned, the contents of which are hereby incorporated by reference.

BACKGROUND OF THE INVENTION

The invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, the prior art stents depicted in FIGS. 1-3 have multiplex cylindrical rings connected by one or more undulating links. While some of these stents are flexible and have the appropriate radial rigidity needed to hold open a vessel or artery, there typically is a tradeoff between flexibility and radial strength and the ability to tightly compress or crimp the stent onto a catheter so that it does not move relative to the catheter or dislodge prematurely prior to controlled implantation in a vessel.

What has been needed and heretofore unavailable is a stent which has a high degree of flexibility so that it can be advanced through tortuous passageways and can be readily expanded, and yet have the mechanical strength to hold open the body lumen or artery into which it is implanted and provide adequate vessel wall coverage. In particular, it would be desirable to have a stent with an end ring configuration that aims at reducing the stent-to-shoulder distance as well as delivering therapeutic drug to the peri-stent area while maintaining a pristine stent deployment. The present invention satisfies these and other needs. That is, the stent of the present invention has a high degree of compressibility to secure it on the catheter and provide a low profile and a high degree of flexibility making it possible to advance the stent easily through tortuous arteries, yet the stent has sufficient radial rigidity so that it can hold open an artery or other blood vessel, or tack up a dissected lining and provide adequate vessel wall coverage.

SUMMARY OF THE INVENTION

The present invention is directed to an intravascular stent that has an inverted cylindrical end ring configuration incorporated into the stent pattern on at least one of a proximal end and a distal end of the stent, which helps in reducing the stent-to-shoulder distance as well as delivering therapeutic drug to the peri-stent area while maintaining a pristine stent deployment. The stent also is highly flexible along its longitudinal axis to facilitate delivery through tortuous body lumens, but which is stiff and stable enough radially in its expanded condition to maintain the patency of a body lumen such as an artery when the stent is implanted therein.

The stent of the present invention generally includes a plurality of cylindrical rings, including a plurality of inverted cylindrical end rings at each stent end, which are interconnected to form the stent. The stent typically is mounted on a balloon catheter if it is balloon expandable or mounted on or in a catheter without a balloon if it is self-expanding.

Each of the cylindrical rings making up the stent have a proximal end and a distal end and a cylindrical plane defined by a cylindrical outer wall surface that extends circumferentially between the proximal end and the distal end of the cylindrical ring. Generally the cylindrical rings have a serpentine or undulating shape which includes at least one U-shaped element, and typically each ring has more than one U-shaped element. The cylindrical rings are interconnected by at least one undulating link which attaches one cylindrical ring to an adjacent cylindrical ring. The undulating links are highly flexible and allow the stent to be highly flexible along its longitudinal axis.

The undulating links may take various configurations but in general have an undulating or serpentine shape. The undulating links can include bends connected by substantially straight portions wherein the substantially straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the cylindrical rings are configured to provide flexibility to the stent in that portions of the rings can flex or bend and tip outwardly as the stent is delivered through a tortuous vessel.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that at least a portion of the undulating links is positioned within one of the valleys and it attaches the valley to an adjacent peak.

While the cylindrical rings and undulating links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resembles such configuration. The U's, W's and Y's promote flexibility in the stent primarily by flexing and by tipping radially outwardly as the stent is delivered through a tortuous vessel.

In one embodiment, the stent includes a plurality of inverted cylindrical end rings coupled at least in part to a plurality of adjacent cylindrical rings on at least one of a proximal end and a distal end of the stent. At least one inverted cylindrical end ring can be a mirror image of at least one corresponding adjacent cylindrical ring such that a symmetrical configuration is present on at least one of the proximal end and the distal end of the stent.

In a further embodiment, it is contemplated by the present invention that at least a portion of the stent may have a variable thickness configuration. For example, the stent may include a combination of rings and links having a variable thickness throughout the length of the stent. Alternatively, select struts of the inverted cylindrical end rings may have a variable thickness while the cylindrical rings and links maintain a standard thickness throughout the length of the stent.

In other embodiments, the inverted cylindrical end rings are shown in combination with various alternative stent patterns. It should be appreciated that the inverted cylindrical end rings of the present invention may be used with virtually any stent design and are not meant to be limited to the designs set forth herein. Accordingly, the resultant shape of the inverted cylindrical end rings will be dependent on the type of stent design used for a particular application. For example, if the cylindrical rings are all U-shaped then the inverted cylindrical end rings likewise can "mirror" that respective shape so that complete symmetry exists on at least one of the proximal end and the distal end of the stent. In yet another embodiment, the inverted cylindrical end rings may assume a different shape than the corresponding adjacent cylindrical rings.

The number and location of undulating links that interconnect adjacent cylindrical rings can be varied as the application requires. Since the undulating links typically do not expand when the cylindrical rings of the stent expand radially outwardly, the links are free to continue to provide flexibility and to also provide a scaffolding function to assist in holding open the artery. Importantly, the addition or removal of the undulating links has very little impact on the overall longitudinal flexibility of the stent. Each undulating link is configured so that it promotes flexibility whereas some prior art connectors actually reduce flexibility of the stent.

The cylindrical rings of the stent are plastically deformed when expanded when the stent is made from a metal that is balloon expandable. Typically, the balloon-expandable stent is made from a stainless steel alloy or similar material.

Similarly, the cylindrical rings of the stent expand radially outwardly when the stent is formed from superelastic alloys, such as nickel-titanium (NiTi) alloys. In the case of superelastic alloys, the stent expands upon application of a temperature change or when a stress is relieved, as in the case of a pseudoelastic phase change.

Because of the undulating configuration of the links, the stent has a high degree of flexibility along the stent axis, which reduces the tendency of stent fishscaling. Stent fishscaling can occur when the stent is bent and portions of the stent project outward when the stent is in the unexpanded condition. The present invention stent with inverted cylindrical end rings reduces the likelihood of fishscaling.

Further, because of the positioning of the links, and the fact that the links do not expand or stretch when the stent is radially expanded, the overall length of the stent is substantially the same in the unexpanded and expanded configurations. In other words, the stent will not substantially shorten upon expansion. The inverted cylindrical end rings of the present invention likewise play a significant role in preventing the substantial shortening of the stent upon expansion due to the ability of the inverted cylindrical end rings to undergo complete expansion when the stent is in an implanted diameter.

In all embodiments, the rings (including the inverted cylindrical end rings) and links may include reservoirs to retain therapeutic drugs. The reservoirs may be formed as either micro-channels or micro-depots within the rings or links. The material of the rings or links associated with these reservoirs may be either a polymer or a metal.

The stent may be formed from a tube by laser cutting the pattern of cylindrical rings, inverted cylindrical end rings, and undulating links, directly in the tube. The stent also may be formed by laser cutting a flat metal sheet in the pattern of the cylindrical rings, inverted cylindrical end rings, and links, and then rolling the pattern into the shape of the tubular stent and providing a longitudinal weld to form the stent.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a prior art stent mounted on a rapid-exchange delivery catheter and positioned within an artery.

FIG. 2 is an elevational view, partially in section, similar to that shown in FIG. 1 wherein the prior art stent is expanded within the artery, so that the stent embeds within the arterial wall.

FIG. 3 is an elevational view, partially in section, showing the expanded prior art stent implanted within the artery after withdrawal of the rapid-exchange delivery catheter.

FIG. 7C is a plan view of the stent of FIG. 7A, which is illustrated in a cylindrical configuration and is tightly crimped or compressed.

FIG. 8C is a plan view of the stent of FIG. 8A, which is illustrated in a cylindrical configuration and is tightly crimped or compressed.

FIG. 9C is a plan view of the stent of FIG. 9A depicting the rings and links, including the inverted end rings, in a crimped or compressed configuration.

FIG. 13 is a plan view of a flattened stent of another embodiment of the invention, which illustrates the pattern of the rings and links, including the inverted end rings.

DETAILED DESCRIPTION OF THE PREFERRED EMBODIMENTS

Figure 4:
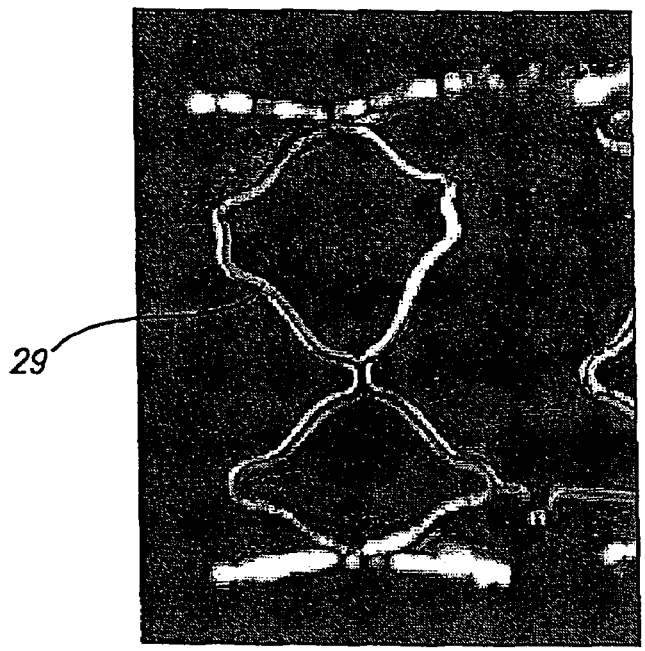
FIG. 4 is a photograph of a three-dimensional view of a prototype stent having inverted cylindrical end rings in a fully expanded diameter.

The present invention stent improves on existing stents by providing a longitudinally flexible stent having a plurality of inverted cylindrical end rings coupled at least in part to a plurality of adjacent cylindrical rings that can be in the form of mirror images of one another such that a symmetrical configuration is present on at least one of a proximal end and a distal end of the stent. In addition to providing longitudinal flexibility, the stent of the present invention also provides radial rigidity and a high degree of scaffolding of a vessel wall, such as a coronary artery. Further, the inverted end ring configuration of the present invention stent aims at reducing the stent-to-shoulder distance as well as delivering therapeutic drugs to the peri-stent area while maintaining a pristine stent deployment.

Before describing in detail an exemplary embodiment of a stent in accordance with the present invention, it is instructive to briefly describe a typical stent implantation procedure and the vascular conditions which are typically treated with stents. Referring now to the drawings, FIG. 1 depicts a prior art stent 10 mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in the coronary arteries, peripheral arteries and other vessels.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the prior art stent expanded and pressed against the vessel wall, and in FIG. 3, the implanted stent remains in the vessel after the balloon has been deflated and the catheter assembly and guide wire have been withdrawn from the patient.

The prior art stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth, which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

The stent patterns shown in FIGS. 1-3 are for illustration purposes only and can vary in size and shape to accommodate different vessels or body lumens. Further, the stent 10 is of a type that can be used in accordance with the present invention.

The inverted cylindrical end ring configuration of the present invention stent can be incorporated into the design of virtually any stent pattern and operates to help reduce the stent-to-shoulder distance. The stent-to-shoulder distance refers to the length that each end of the stent extends relative to the tapered shoulder region of the expandable member or balloon. The shoulder 28 (FIG. 2) of the balloon 22 is typically tapered in design at each end of the balloon with a balloon working length 31 formed therebetween. Accordingly, a negative stent-to-shoulder distance is created if the end rings extend beyond the balloon working length and into the balloon tapered shoulder region. The present invention stent benefits from having a negative stent-to-shoulder distance as will be set forth in further detail below. On the other hand, a positive stent-to-shoulder distance is created if the stent end rings remain within the balloon working length. This is typically the case of a stent without the inverted end rings of the present invention stent.

Figure 5:
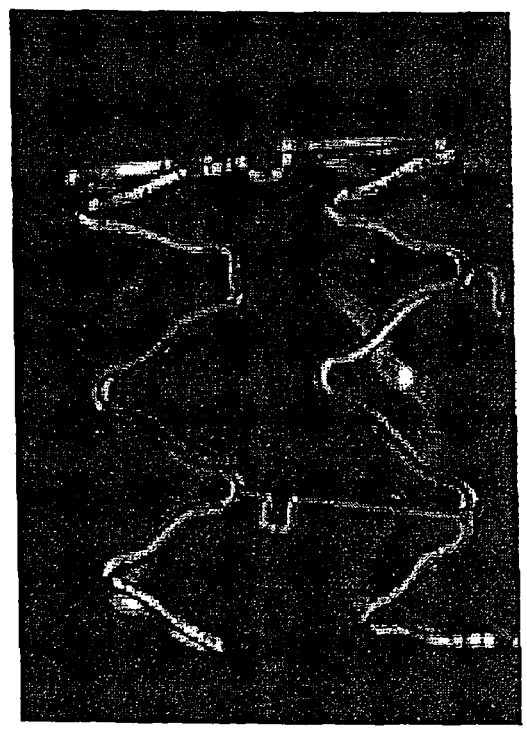
FIG. 5 is a photograph of a three-dimensional view of a stent without inverted cylindrical end rings in an expanded diameter.
Figure 6A:
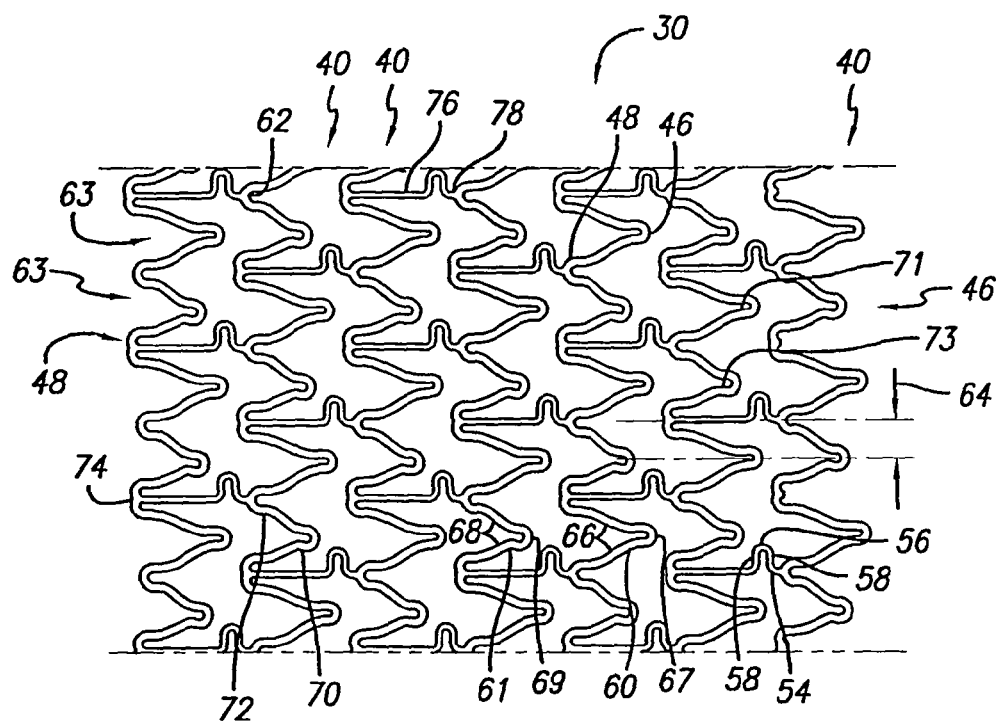
FIG. 6A is a plan view of a flattened stent, which illustrates the pattern of the rings and links without the inverted end rings of the present invention.
Figure 6B:
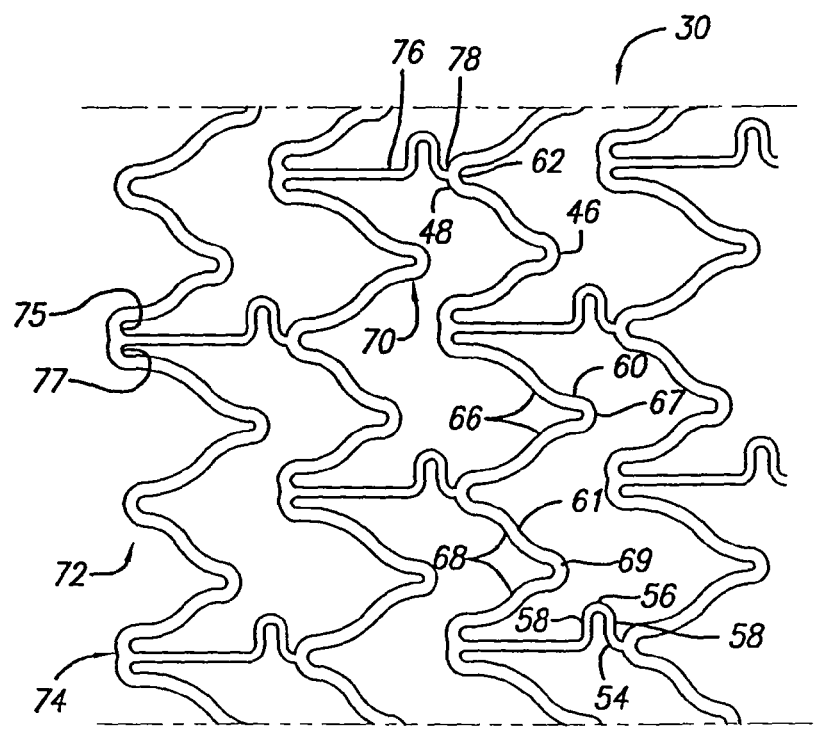
FIG. 6B is a partial plan view of the stent of FIG. 6A, which has been expanded to approximately 3.0 mm inside diameter.
Figure 6C:
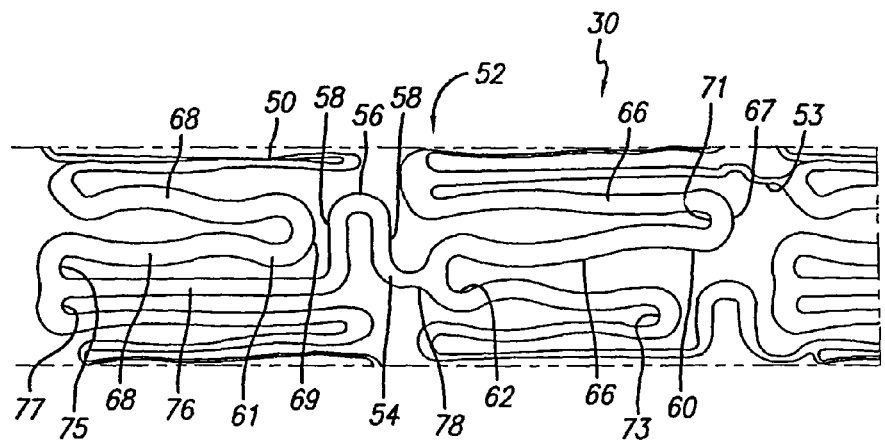
FIG. 6C is a plan view of a portion of the stent of FIG. 6A rolled into a cylindrical configuration and tightly crimped so that the various stent struts are either in close contact or contacting each other.

More specifically, in studies performed on a prototype with inverted cylindrical end rings incorporated therein and based on the design of the VISION® stent, manufactured by Advanced Cardiovascular Systems, Inc., of Santa Clara, Calif., it was demonstrated that the stent length of 21 mm remained unchanged both before and after expansion of the respective stent. With the expansion of the stent, the inverted cylindrical end rings extend beyond the balloon working length thereby creating a negative stent-to-shoulder distance 29 (FIG. 4) of about −0.3 mm. FIG. 4 illustrates the inverted cylindrical end rings of the stent in a fully expanded diameter. In comparative studies performed on a VISION® stent without inverted cylindrical end rings cut to a length of 20.2 mm, it was demonstrated that the stent experienced shortening after expansion and resulted in a stent length of 19.5 mm, a length change of −0.7 mm. This same stent without inverted cylindrical end rings yielded a positive stent-to-shoulder distance of about 0.4 mm. FIG. 5 illustrates the stent without the inverted cylindrical end rings of the present invention stent in an expanded diameter. It is apparent that the cylindrical rings at each stent end of the stent shown in FIG. 5 are not completely expanded to the extent of the inverted cylindrical end rings of the stent shown in FIG. 4. Accordingly, the incorporation of inverted cylindrical end rings into a particular stent design provides the stent with the ability to effect a complete expansion. Further, the incorporation of inverted cylindrical end rings into a particular stent design results in the stent having a pristine deployment and a consistent stent length after expansion.

In keeping with the present invention, FIGS. 6-15 depict stent 30 in various configurations. Referring to FIG. 6A, for example, stent 30 is shown in a flattened condition (without the inverted cylindrical end rings of the present invention) so that the pattern can be clearly viewed, even though the stent is in a cylindrical form in use, such as shown in FIG. 6C. The stent is typically formed from a tubular member, however, it can be formed from a flat sheet such as shown in FIG. 6A and rolled into a cylindrical configuration as shown in FIG. 6C. FIG. 6B illustrates a partial plan view of the stent of FIG. 6A expanded to approximately 3.0 mm inside diameter of the stent.

As shown in FIGS. 6-15, stent 30 is made up of a plurality of cylindrical rings 40 which extend circumferentially around the stent when it is in a tubular form. The stent has a delivery diameter 42 (FIG. 7C) and an implanted diameter 44 (FIG. 7B). Each cylindrical ring 40 has a cylindrical ring proximal end 46 and a cylindrical ring distal end 48. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 40 defines a cylindrical plane 50, which is a plane defined by the proximal and distal ends 46, 48 of the ring and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

With further reference to FIGS. 6-15, undulating link 54 is positioned within cylindrical plane 50. The undulating links connect one cylindrical ring 40 to an adjacent cylindrical ring 40 and contribute to the overall longitudinal flexibility to the stent due to their unique construction. The flexibility of the undulating links derives in part from curved portion 56 connected to straight portions 58 wherein the straight portions are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

Referring to FIGS. 6-11, the stent 30 can be described more particularly as having a plurality of first peaks 60, second peaks 61, and valleys 62. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery. As can be seen, for example, in FIG. 6A, peaks 60, 61 are in phase 63, meaning that the peaks 60, 61 point in the same direction and are substantially aligned along the longitudinal axis of the stent. It may be desirable under certain circumstances to position the peaks so that they are out of phase, that is, the peaks of one ring would be circumferentially offset from the peaks of an adjacent ring so that the apex of adjacent peaks pointed toward each other. This out of phase configuration is shown in FIGS. 7-11, and 13-15, with respect to the configuration of the inverted cylindrical end rings 82 and the adjacent cylindrical rings 40. As shown in FIGS. 6-15, the peaks are circumferentially offset 64 from the valleys and from the undulating link 54. Positioning the peaks, valleys, and undulating links in this manner, provides a stent having uniform expansion capabilities, high radial strength, a high degree of flexibility, and sufficient wall coverage to support the vessel.

It should be appreciated that the stent patterns shown in FIGS. 6-15 are for illustration purposes only and can vary in shape and size to accommodate different vessels or body lumens. Thus, rings 40 connected by links 54 can have any structural shape and are not limited to the aforedescribed undulating rings. Links connecting the rings can also include oscillating patterns, sinusoidal patterns and zig-zag patterns.

Figure 7A:
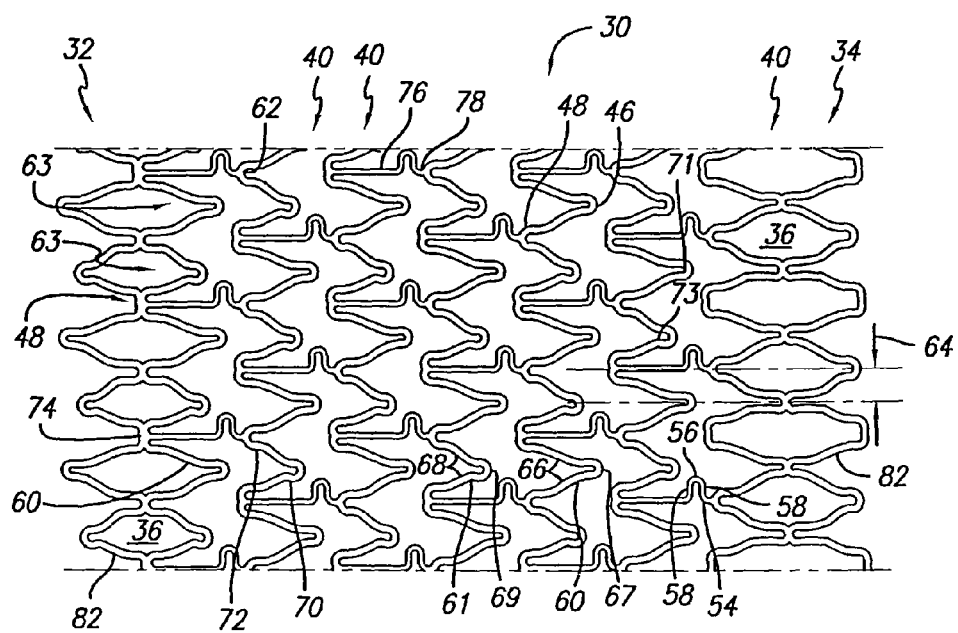
FIG. 7A is a plan view of a flattened stent of another embodiment of the invention, which illustrates the pattern of the rings and links, including the inverted end rings.
Figure 7B:
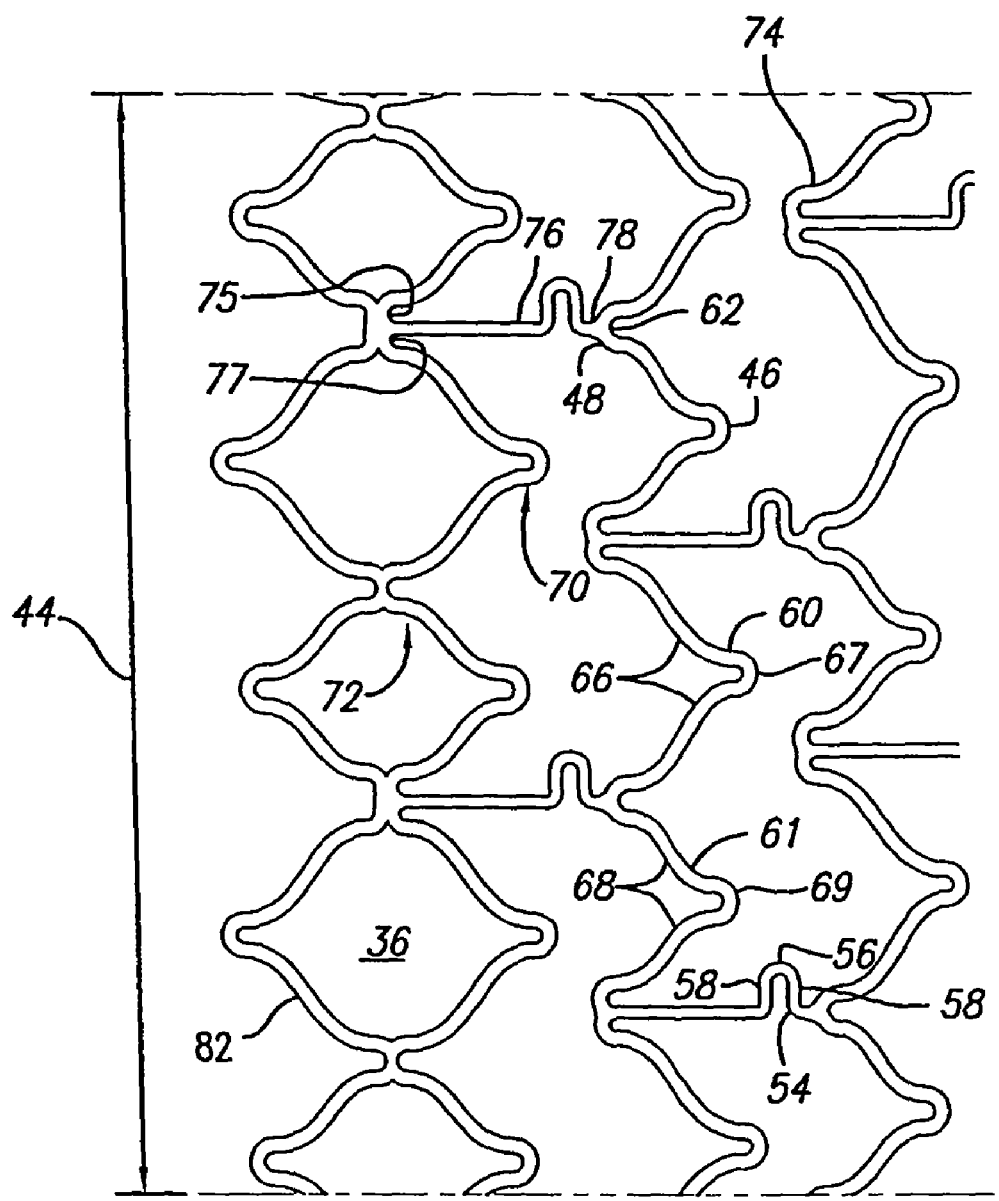
FIG. 7B is a partial plan view of the stent of FIG. 7A, which has been expanded to approximately 3.0 mm inside diameter.

For illustration purposes, one exemplary embodiment of the stent 30 of the present invention is shown in FIGS. 7A-7C. In particular, a plurality of inverted cylindrical end rings 82 are coupled at least in part to a plurality of adjacent cylindrical rings 40 on at least one of a proximal end 32 and a distal end 34 of the stent. At least one inverted cylindrical end ring is a mirror image of at least one corresponding adjacent cylindrical ring such that a symmetrical configuration 36 is present on at least one of the proximal end 32 and the distal end 34 of the stent. The resultant shape of the inverted cylindrical end rings may be dependent on the type of stent design used for a particular application. Thus, for example, if the cylindrical rings include U-shaped portions and W-shaped portions, then the inverted cylindrical end rings likewise can "mirror" those respective shapes such that complete symmetry exists on at least one of the proximal end and the distal end of the stent.

Figure 7D:
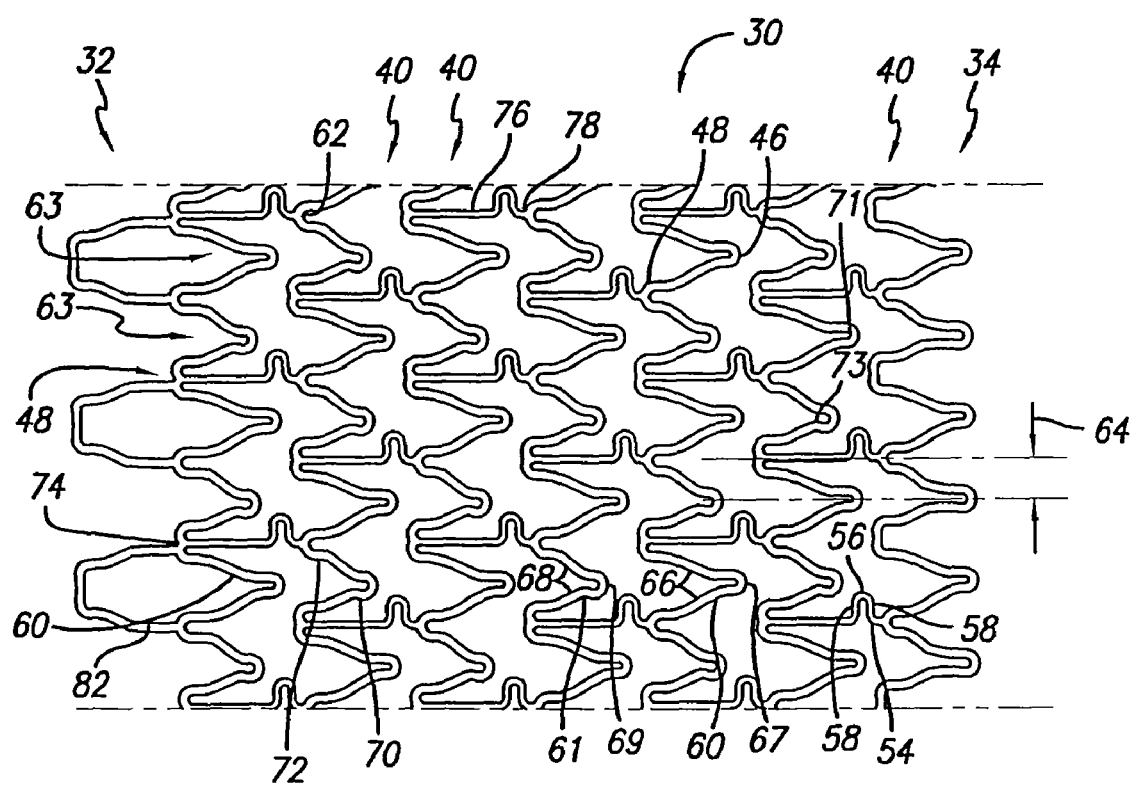
FIG. 7D is a plan view of a flattened stent of another embodiment of the invention, which illustrates the different patterns of the inverted end rings and the adjacent rings positioned at the proximal end of the stent.
Figure 8A:
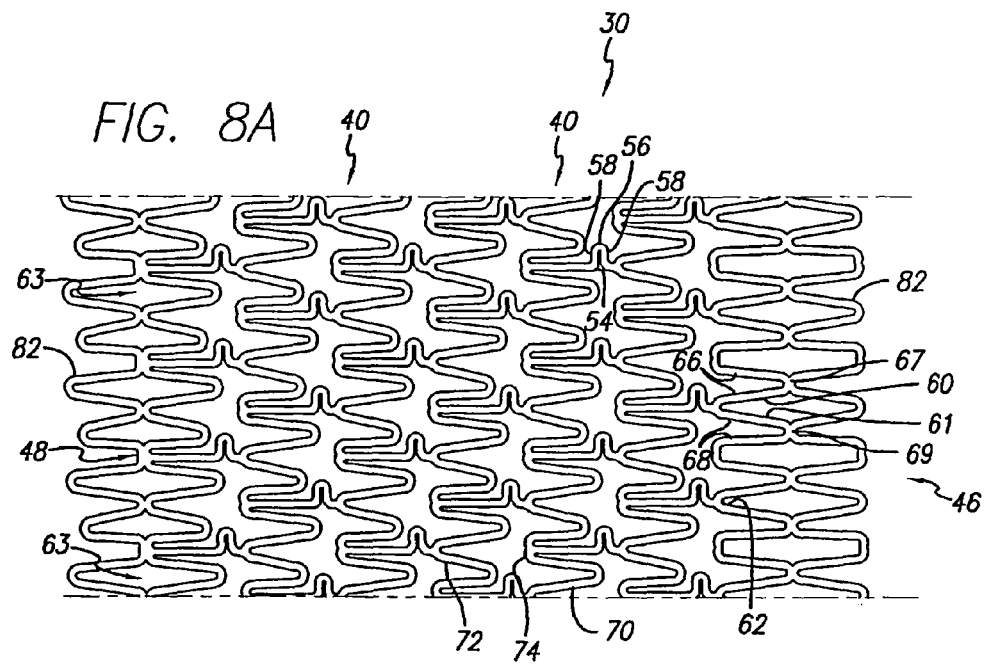
FIG. 8A is a plan view of a flattened stent of another embodiment of the invention, which illustrates the pattern of the rings and links, including the inverted end rings.
Figure 8B:
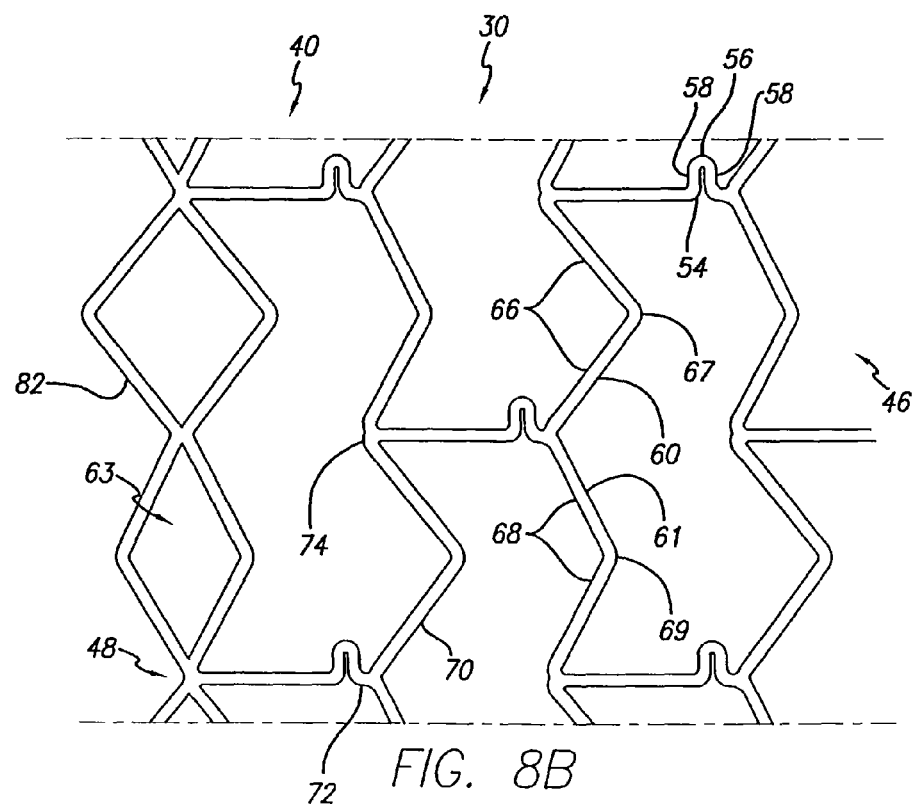
FIG. 8B is a partial plan view of the stent of FIG. 8A, which has been expanded to approximately 4.0 mm inside diameter.

In another embodiment shown in FIG. 7D, it is contemplated by the invention that the plurality of inverted cylindrical end rings 82 can assume a different shape from that of the corresponding plurality of adjacent cylindrical rings 40 while positioned on at least one of the proximal end 32 and the distal end 34 of the stent. It is further contemplated by the present invention that the inverted cylindrical end rings can assume virtually any structural undulating shape.

It is contemplated by the present invention that the symmetrical configuration 36 is present on at least one of the proximal end 32 and the distal end 34 of the stent 30 when the first peaks 60 of the inverted cylindrical end rings 82 and the adjacent cylindrical rings 40 are coupled at least in part to each other in the form of a mirror image. Similarly, the symmetrical configuration is present on at least one of the proximal end and the distal end of the stent when the second peaks 61 of the inverted cylindrical end rings and the adjacent cylindrical rings are coupled at least in part to each other in the form of a mirror image. The coupling of the first peaks and the second peaks of the inverted cylindrical end rings and the adjacent cylindrical rings to each other, respectively, occurs by laser cutting a pattern of a particular stent design into tubing, or a flat sheet, which is then rolled up in a cylindrical configuration with the longitudinal edges welded to form a cylindrical member, as further described below. The plurality of inverted cylindrical end rings are configured to be completely expanded at about 95% up to about 100% of the inside diameter of the stent.

In keeping with the invention, and as shown in FIGS. 6-11, each of the cylindrical rings has a plurality of first peaks 60 which have first struts 66 attached to a first apex 67. The first struts can be either curved or straight depending upon the particular application. The cylindrical rings also have second peaks 61 which have second struts 68 attached to a second apex 69. Again, the second struts can be either curved or straight depending upon the particular application. Importantly, the length of the second struts 68 is shorter than the length of the first struts 66. As can be seen in FIGS. 6C, 7C, 8C, and 9C, when the stent is in a crimped condition, or a partially crimped condition, the first struts and second struts respectively will be closer to each other when the stent is compressed or crimped onto the balloon or expandable member of the catheter. The crimping or compressing process, however, also moves the undulating link 54 along with its curved portion 56 closer to the second peak. In order to allow the stent to be more tightly crimped onto the balloon portion of the catheter, and to avoid overlapping between the undulating link and the second peak, the second struts 68 are shorter than the first struts 66, thus avoiding any overlapping contact between the curved portion of the undulating link and the second peak. The various stent struts, curved portions, links, and peaks and valleys may contact each other when the stent is crimped or compressed, but overlapping is an undesirable feature.

More particularly, in order to more tightly crimp or compress the cylindrical rings 40 of the stent 30, the undulating link 54 is tightly crimped or compressed into contact with, or near contact with, second peak 61. As can be seen, for example, in FIG. 7C, curved portion 56 and straight portions 58 are in close relation to second peak 61 and are either in contact (not shown) or near contact with second apex 69. The curved portion is proximal to the second peak and the various struts in each of the rings are tightly compressed to be in contact or near contact with each other. For example, first struts 56 and second struts 58 as well as arm 76 of the undulating link all are in close contact, or contact with each other, in order to provide a very low profile, tightly crimped stent onto the balloon portion of the catheter. Likewise, if the stent is formed of a self-expanding material such as nickel-titanium, the stent will similarly be tightly crimped and positioned within a sheath or within the catheter for delivery in the vascular system. Importantly, the curved portion and the straight portions of the undulating link are positioned relative to the second peak to allow the stent to be tightly crimped as described.

Referring to FIGS. 6-11, the stent 30 of the invention also can be described as having cylindrical rings formed of U-shaped portions 70, Y-shaped portions 72, and W-shaped portions 74. Again, while the stent is generally laser cut from a tube and it typically has no discreet parts, for ease of identification the stent of the invention also can be referred to as having U-, Y-, and W-shaped portions. The U-shaped portions have no supporting structure attached thereto. The Y-shaped portions, at their base, or apex, have arm 76 extending therefrom which is attached to undulating link 54. The W portion has at its base or curve portion an arm 78 which attaches at the other end of the undulating link. The length of the arms attaching the links to the rings can vary.

Due to the intricate patterns as disclosed in FIGS. 6-11, the rate of expansion of the various portions of the stent, including the U-shaped portion 70, the Y-shaped portion 72, and the W-shaped portion 74, can vary. Accordingly, one aspect of the invention provides for different radii of curvature at various points so that the stent will expand evenly and uniformly. Thus, first radius 71 which corresponds with first peak 60 has a smaller radius of curvature than second radius 72 which corresponds with second peak 61. Generally, the longer the struts associated with a peak, the more easily that portion of the stent will expand, so that a smaller radius is associated with peaks having longer struts. Likewise, for peaks, such as second peak 61, which has struts 68 that are shorter than the struts 66 of first peak 60, a greater radius of curvature is present which will expand more easily in order to compensate for the stiffer bending moments created by the shorter struts 68.

Also referring to FIGS. 6-11, the radius of curvature of the various portions of the W-shaped portion also varies to provide uniform stent expansion. Since the second peak 61 and its associated struts 68 have a tendency to expand more slowly as the stent is expanded, a greater radius of a curvature is provided in the adjacent part of the W-shaped portion 74. Thus, third radius 75 of the W-shaped portion 74 is greater than the fourth radius 77 in the W-shaped portion. The third radius 75 is adjacent to second peak 61 which has a tendency to expand more slowly, while fourth radius 77 is adjacent the first peak 60 which has a tendency to expand more easily. By varying the radii of curvature in the W-shaped portion, the stent will expand more evenly and compensate for the varying rates of expansion of adjacent portions in a cylindrical ring.

Figure 9A:
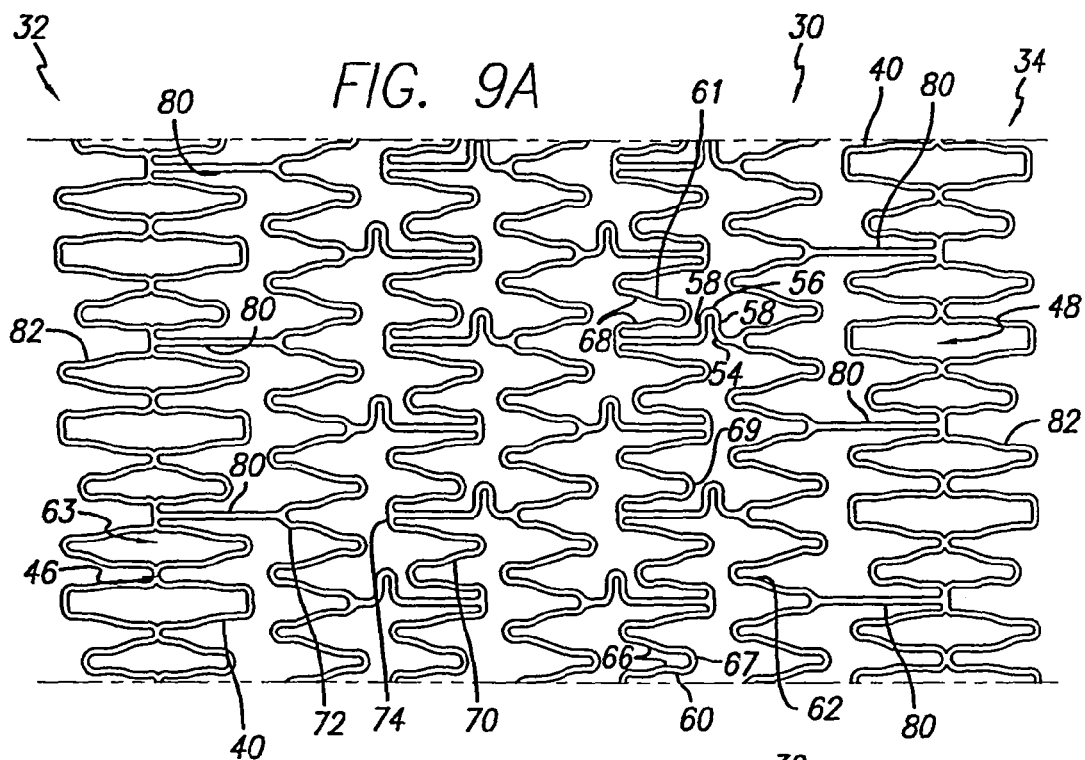
FIG. 9A is a plan view of a flattened stent of another embodiment of the invention, which illustrates the pattern of the rings and links, including the inverted end rings.

It is also a design feature that more or fewer undulating links 54 will be positioned between adjacent cylindrical rings 40. Further, in order to increase stent stability, straight links 80, as shown in FIG. 9A, in addition to undulating links 54, connect adjacent cylindrical rings. The straight links will provide stability and assist in preventing stent foreshortening, as do the undulating links. Further, the straight links may provide more rigidity in a localized area, such as at the stent ends, such that it may be desirable to incorporate more straight links between the cylindrical rings at the stent ends than in the center of the stent. The straight links used in conjunction with the inverted cylindrical end rings 82 of the present invention provide enhanced rigid connections at both the proximal end 32 and the distal end 34 of the stent.

Figure 9B:
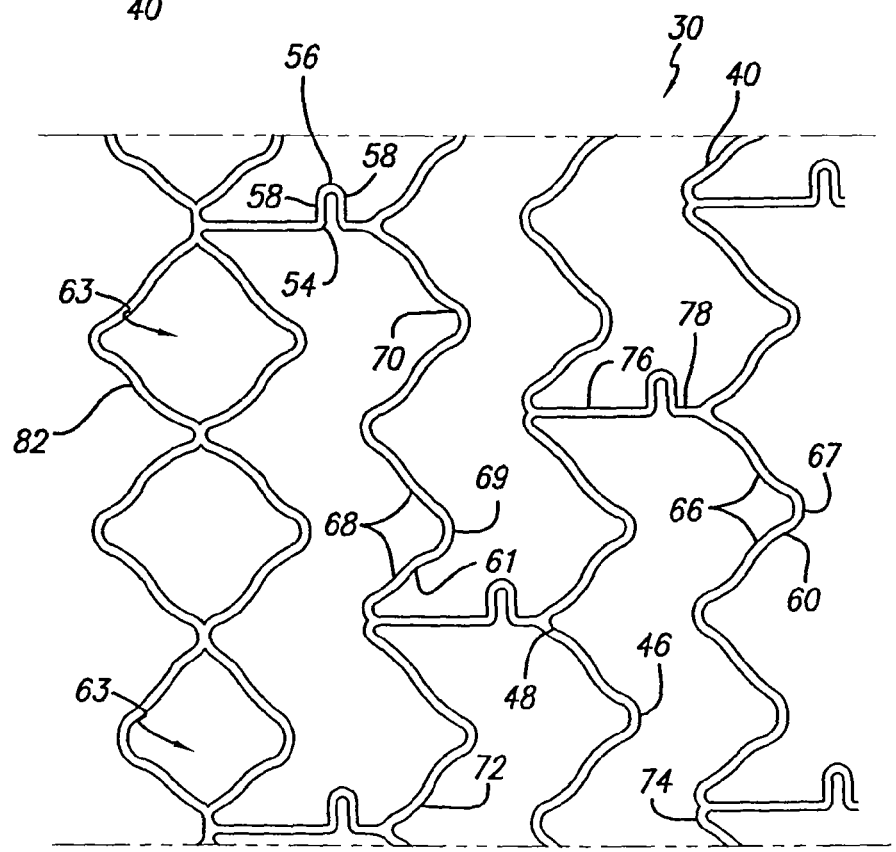
FIG. 9B is a partial plan view of the stent of FIG. 9A, which has been expanded to approximately 4.0 mm inside diameter.
Figure 10:
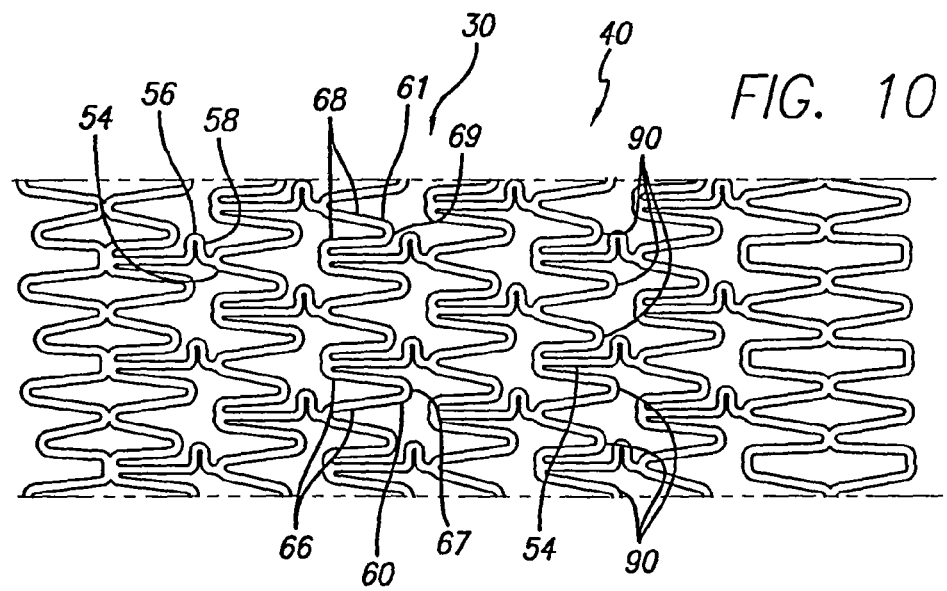
FIG. 10 is a plan view of a flattened stent of another embodiment of the invention, which illustrates the pattern of the rings and links, including the inverted end rings.
Figure 11:
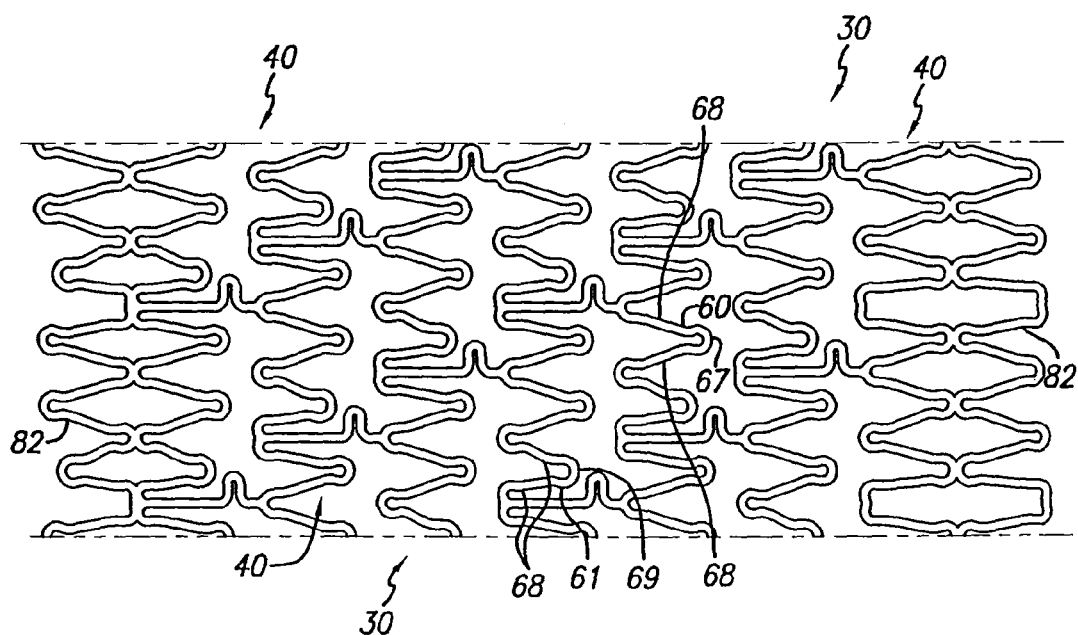
FIG. 11 is a plan view of a flattened stent of another embodiment of the invention, which illustrates the pattern of the rings and links, including the inverted end rings.

FIG. 9 is another exemplary embodiment of a particular stent design incorporating the inverted cylindrical end rings 82 of the present invention to enhance the mechanical properties of the stent. The stent 30 is similar to the other embodiments except that the radius of curvature of all of the peaks and valleys are somewhat larger in order to make it easier to laser cut the stent pattern from a tubular member or from a flat sheet. As the stent expands, the peak having a greater radius of curvature will expand more easily than those having a smaller radius of curvature, thus, compensating for the length of the struts in which the peaks having shorter struts have a tendency to expand more slowly than peaks having longer struts and which have moment arms that bend more easily.

In one aspect of the invention, after stent 30 is implanted in a coronary artery, or other vessel, because of its novel design, the cylindrical rings 40 have the ability to flex radially as the vessel pulsates when blood pumps through it. Likewise, because of the novel and unique design of undulating links 54, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

Figure 12:
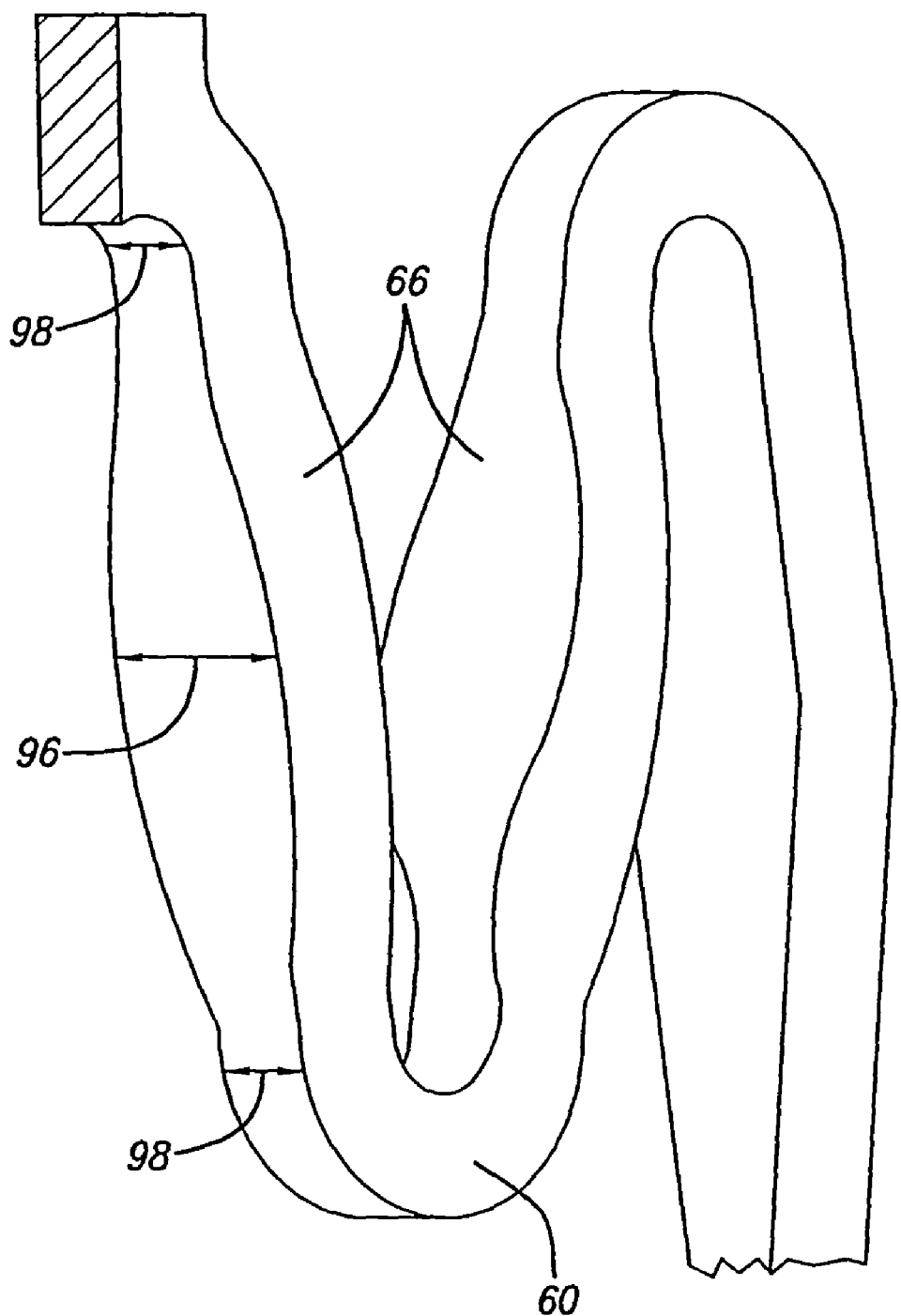
FIG. 12 is an enlarged partial perspective view of a portion of a peak and associated struts depicting variable thickness struts.
Figure 14:
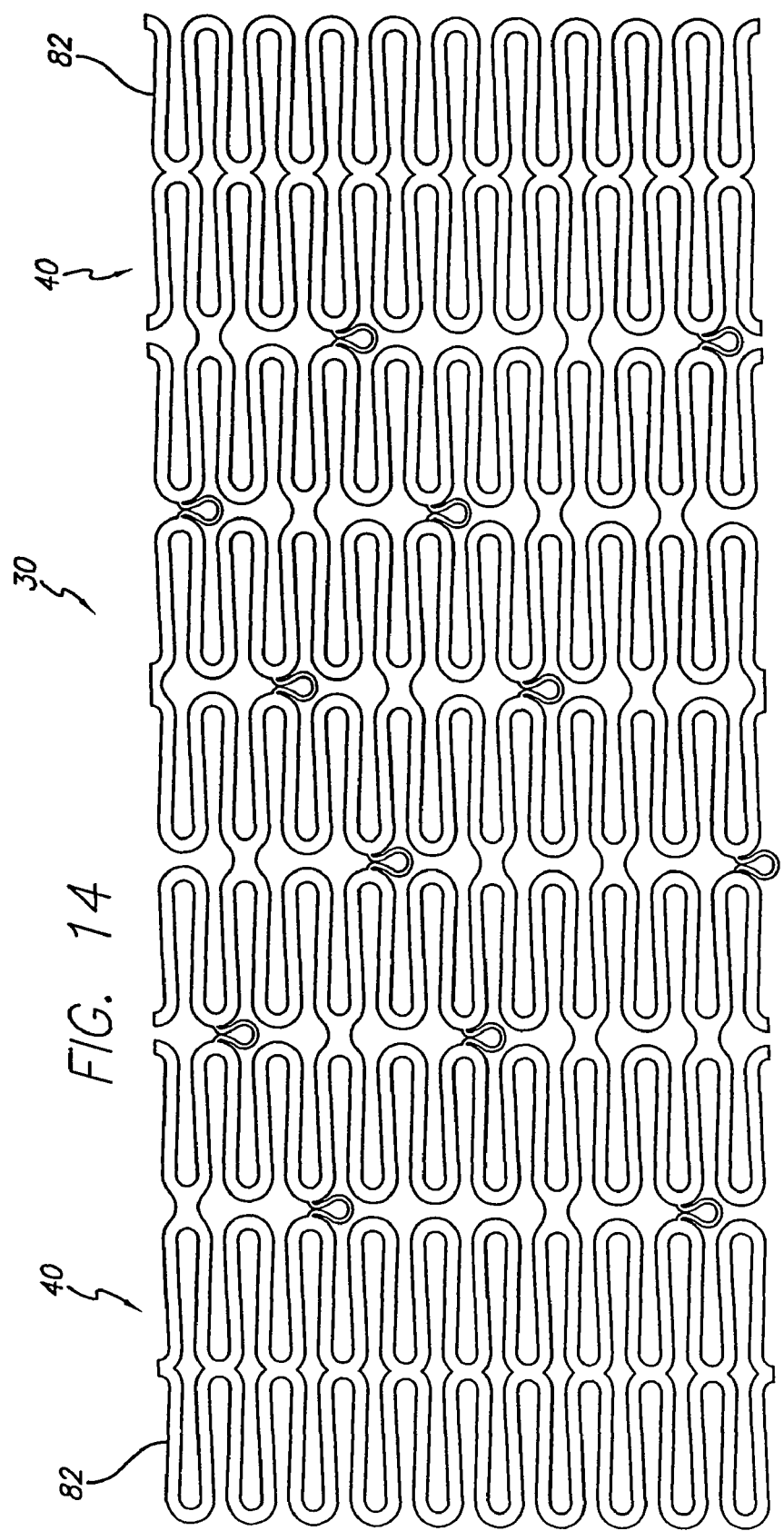
FIG. 14 is a plan view of a flattened stent of another embodiment of the invention, which illustrates the pattern of the rings and links, including the inverted end rings.

In another aspect of the invention, the stent 30 is formed so that the various struts of the cylindrical rings, including the U-shaped portions 70, Y-shaped portions 72, W-shaped portions 74, and the undulating links 54, all can be formed so that each has a variable thickness along the stent length. For example, the undulating link, and its associated arms 76, 78 may be thicker at one end (arm 76) than at the other end of the link (arm 78). Further, first struts 66 and second struts 68 may vary in thickness (radial thickness) along their length in order to create variable flexibility in the rings. As shown in FIG. 12, first peak 60 has first struts 66 that have radial thick portion 96 in the middle of the struts and radial thin portion 98 near the ends of the struts. As another example, the rings at for example the proximal end of the stent may be thicker radially than the rings in the center of the stent. A variable thickness stent would benefit from being used in conjunction with the inverted cylindrical end rings 82 of the present invention to provide increased rigid connections between the last two rings at both the proximal end 32 and the distal end 34 of the stent. Further, it is contemplated by the present invention that select struts of the inverted cylindrical end rings may have a variable thickness while the cylindrical rings and links maintain a standard thickness throughout the length of the stent. Other combinations of variable thickness struts can be used on the rings and links within the stent and can be incorporated into the other embodiments as desired.

FIGS. 10-11 and 13-14 illustrate alternative stent patterns that may be used in combination with the inverted stent ring 82 configuration of the present invention. Regardless of which stent pattern is ultimately used in a particular application, the present invention contemplates that the inverted cylindrical end rings have the ability to mirror the respective shape of the adjacent cylindrical rings such that complete symmetry exists on at least one of the proximal end and the distal end of the stent. This mirror-like arrangement of the inverted cylindrical rings and corresponding adjacent plurality of cylindrical rings enhances the ability of the stent to effect a complete expansion within the body lumen for subsequent treatment thereto. As mentioned earlier, a similar effect (i.e., complete expansion of stent) is achieved when the inverted cylindrical end rings assume a different shape from that of the corresponding adjacent cylindrical rings.

Figure 15:
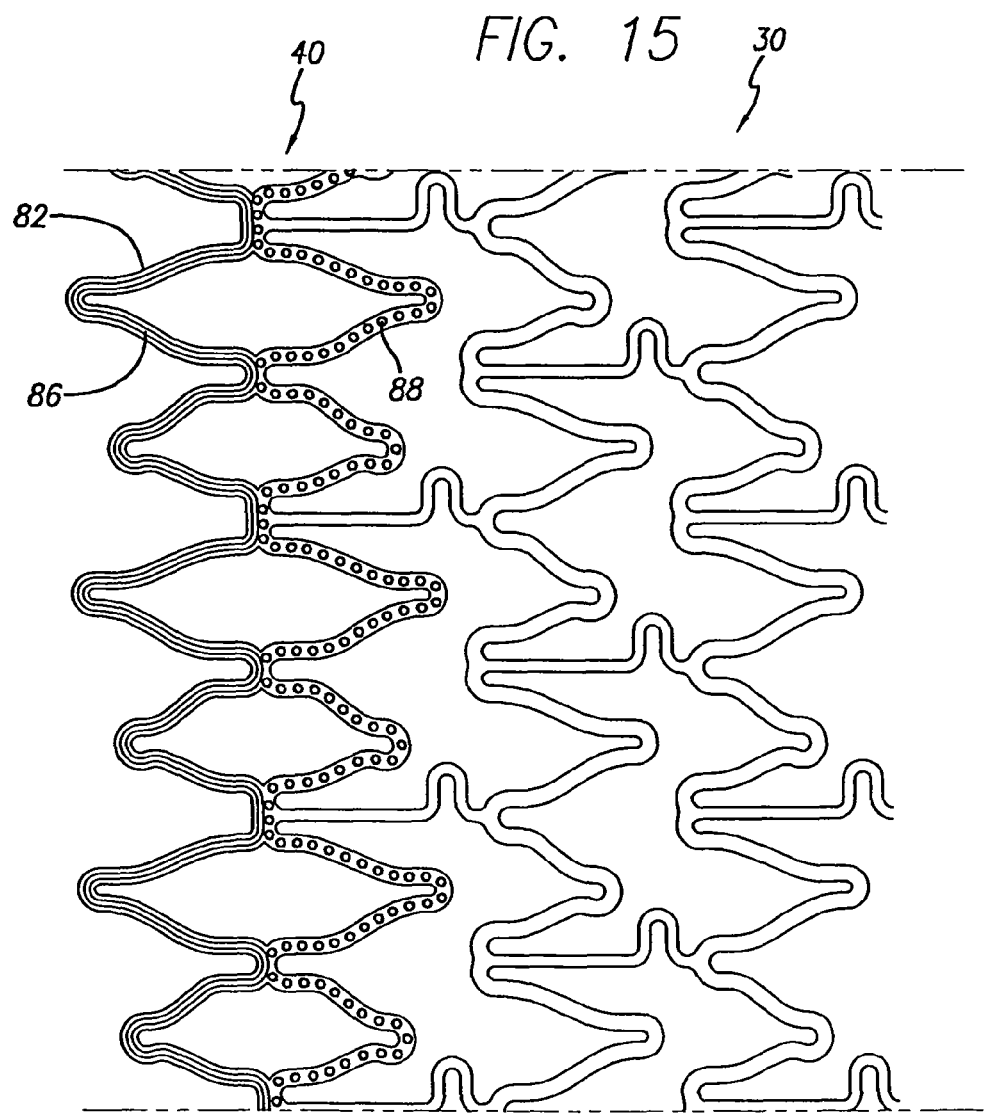
FIG. 15 is an enlarged partial view of a flattened section of one embodiment of the invention incorporating inverted cylindrical end rings and adjacent cylindrical rings with micro-channels and micro-depots.

In another embodiment of the present invention shown in FIG. 15, therapeutic drugs can be uniformly loaded and distributed through reservoirs formed in the struts of the inverted cylindrical end rings 82 to help prevent restenosis within the peri-stent area of the stent 30. More particularly, the struts of the inverted cylindrical end rings incorporate micro-channels 86 and/or depots 88 within their structure to help retain the therapeutic drug. For illustration purposes, both types of reservoirs are shown in the embodiment of FIG. 15 while in practice either or both may be incorporated into the design of the stent. Additionally, either type of reservoir can be used on other rings within the stent and can be incorporated into the other embodiments as desired.

The stent 30 of the present invention can be mounted on a balloon catheter similar to that shown in the prior art device in FIG. 1. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient and the stent remains implanted in the artery. Similarly, if the stent of the present invention is made from a self-expanding metal alloy, such as nickel-titanium or the like, the stent may be compressed or crimped onto a catheter and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter or the catheter is withdrawn proximally and the stent held in place until it exits the catheter and self-expands into contact with the wall of the artery. Balloon catheters and catheters for delivering self-expanding stents are well known in the art.

The rings, inverted cylindrical end rings, and the links, may be made of a suitable biocompatible material such as stainless steel, titanium, tungsten, tantalum, vanadium, cobalt chromium, gold, palladium, platinum, and iradium, as well as high strength thermoplastic polymers. The inverted cylindrical end rings have a strut thickness and width ranging from about 0.0024 inch (0.0610 mm) up to about 0.0034 inch (0.0864 mm). The stent diameters are very small, so the tubing from which they are made also has a small diameter. For PTCA applications, typically the stent has an outer diameter on the order of about 1.65 mm (0.065 inch) in the unexpanded condition, the same outer diameter of the tubing from which it is made, and can be expanded to an outer diameter of 5.08 mm (0.2 inch) or more. The wall thickness of the tubing is about 0.076 mm (0.003 inch). In the case of forming the stent from cobalt-chromium the wall thickness of the tubing may be reduced. For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

The rings may also be made of materials such as superelastic (sometimes called pseudoelastic) nickel-titanium (NiTi) alloys. In this case the rings would be formed full size but deformed (e.g., compressed) to a smaller diameter onto the balloon of the delivery catheter to facilitate intraluminal delivery to a desired intraluminal site. The stress induced by the deformation transforms the rings from an austenite phase to a martensite phase, and upon release of the force when the stent reaches the desired intraluminal location, allows the stent to expand due to the transformation back to the more stable austenite phase. The NiTi alloy rings may be attached to the other rings through welding, bonding and other well known types of attachments.

The stent of the invention also can be coated with a drug or therapeutic agent. The presence of the inverted cylindrical end rings incorporated into the design of the stent of the invention enhances delivery of therapeutic drug to the peristent area. Further, it is well known that the stent (when both the rings and links are made from metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Representative examples of polymers that can be used to coat a stent in accordance with the present invention include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolicacid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; polybutylmethacrylate; rayon; rayon-triacetate; poly(glycerol-sebacate); cellulose acetate; cellulose butyrate; cellulose acetate butyrate; cellophane; cellulose nitrate; cellulose propionate; cellulose ethers; and carboxymethyl cellulose.

"Solvent" is a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM), iso-propylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, pentane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof. The therapeutic substance contained in the coating can be for inhibiting the activity of vascular smooth muscle cells. More specifically, the therapeutic substance can be aimed at inhibiting abnormal or inappropriate migration and/or proliferation of smooth muscle cells for the inhibition of restenosis. The therapeutic substance can also include any active agent capable of exerting a therapeutic or prophylactic effect in the practice of the present invention. For example, the therapeutic substance can be for enhancing wound healing in a vascular site or improving the structural and elastic properties of the vascular site.

Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. Furthermore, the calculation of dosages, dosage rates and appropriate duration of treatment are previously known in the art.

The stent of the present invention can be made in many ways. One method of making the stent is to cut a tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biocompatible surface active agent. Other electropolishing solutions are well known in the art. The stents may be further treated if desired, for example, by applying a biocompatible coating.

Other methods of forming the stent of the present invention can be used, such as chemical etching, electric discharge machining, laser cutting a flat sheet and rolling it into a cylinder, and the like, all of which are well known in the art at this time.

The stent of the present invention also can be made from metal alloys other than stainless steel, such as shape memory alloys. Shape memory alloys are well known and include, but are not limited to, nickel-titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, can be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, connection of inverted end rings to end rings, materials used, and the like have been described herein and are provided as examples only. Other modifications and improvements may be made without departing from the scope of the invention.

What is claimed:

1. A flexible intravascular stent for use in a body lumen, comprising:
    a plurality of cylindrical rings aligned along a common longitudinal axis and interconnected to form the stent, each cylindrical ring having a first delivery diameter and a second implanted diameter;
    each cylindrical ring having a plurality of first peaks and second peaks, each of the peaks having a height, the second peaks being shorter than the first peaks;
    at least one undulating link attaching each cylindrical ring to an adjacent cylindrical ring, the undulating links having a curved portion extending transverse to the stent longitudinal axis toward the second peak, the height of the second peak being sized so that as the stent is compressed to the first delivery diameter, the curved portion is positioned proximal to the second peak;
    wherein a plurality of inverted cylindrical end rings are coupled at least in part to a plurality of adjacent cylindrical rings on at least one of a proximal end and a distal end of the stent, at least one inverted cylindrical end ring being a mirror image of at least one corresponding adjacent cylindrical ring such that a symmetrical configuration is present on at least one of the proximal end and the distal end of the stent; wherein the symmetrical configuration is present on at least one of the proximal end and the distal end of the stent when the first peaks of the inverted cylindrical end rings and the adjacent cylindrical rings are coupled at least in part to each other in the form of a mirror image.

2. The stent of claim 1, wherein the symmetrical configuration is present on at least one of the proximal end and the distal end of the stent when the second peaks of the inverted cylindrical end rings and the adjacent cylindrical rings are coupled at least in part to each other in the form of a mirror image.

3. The stent of claim 1, wherein the symmetrical configuration is present on both the proximal end and the distal end of the stent.

* * * * *